US006970732B2

(12) United States Patent
Winston et al.

(10) Patent No.: US 6,970,732 B2
(45) Date of Patent: *Nov. 29, 2005

(54) METHOD FOR GUIDING A MEDICAL INSTRUMENT THROUGH A BODY

(75) Inventors: Thomas R. Winston, Leawood, KS (US); John M. Neet, Lawrence, KS (US)

(73) Assignee: Intraluminal Therapeutics, Inc., Carlsbad, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 10/265,801

(22) Filed: Oct. 7, 2002

(65) Prior Publication Data

US 2003/0050562 A1 Mar. 13, 2003

Related U.S. Application Data

(60) Division of application No. 09/276,379, filed on Mar. 25, 1999, now Pat. No. 6,463,313, which is a continuation of application No. 08/890,631, filed on Jul. 9, 1997, now Pat. No. 6,048,349.

(51) Int. Cl.$^7$ .............................................. A61B 6/00
(52) U.S. Cl. ...................... 600/407; 600/478; 600/437; 356/477
(58) Field of Search ............................. 600/407, 427, 600/437, 478; 356/477

(56) References Cited

U.S. PATENT DOCUMENTS

| | | | |
|---|---|---|---|
| 5,217,018 A | * | 6/1993 | Dias ............................ 600/463 |
| 5,383,467 A | * | 1/1995 | Auer et al. .................. 600/342 |
| 5,582,171 A | * | 12/1996 | Chornenky et al. ......... 600/425 |
| 5,921,926 A | * | 7/1999 | Rolland et al. .............. 600/407 |
| 5,951,482 A | * | 9/1999 | Winston et al. ............. 600/476 |
| 6,048,349 A | * | 4/2000 | Winston et al. ............. 606/108 |
| 6,463,313 B1 | * | 10/2002 | Winston et al. ............. 600/407 |

* cited by examiner

Primary Examiner—Ruth S. Smith
(74) Attorney, Agent, or Firm—Armstrong Teasdale LLP

(57) ABSTRACT

Guidance systems for guiding a catheter through tissue within a body are described. In one form, the system is implemented in connection with a catheter which includes a catheter body having a optic fibers extending between a first end and a second end thereof. The guidance system is coupled to the catheter body and includes a first optic fiber, a second optic fiber, and a detecting element. The first optic fiber includes a first end and a second end, and is coupled to the catheter body so that the first optic fiber second end is adjacent the catheter second end. The second optic fiber also includes a first end and a second end, and a reference mirror is positioned adjacent the second optic fiber second end. The first optic fiber first end is communicatively coupled to the detecting element and the second optic fiber first end is communicatively coupled to the detecting element. The detecting element is configured to determine interference between a light beam propagating through the first optic fiber and a light beam propagating through the second optic fiber.

14 Claims, 2 Drawing Sheets

METHOD FOR GUIDING A MEDICAL INSTRUMENT THROUGH A BODY

This application is a divisional of U.S. application Ser. No. 09/276,379, filed Mar. 25, 1999, now U.S. Pat. No. 6,463,313, which is a continuation of U.S. application Ser. No. 08/890,631, filed Jul. 9, 1997, now U.S. Pat. No. 6,048,349, both of which are hereby incorporated by reference.

FIELD OF THE INVENTION

This invention relates generally to medical instruments and, more particularly, to systems and methods for guiding medical instruments through a body or a portion of the body, such as a blood vessel.

BACKGROUND OF THE INVENTION

Disease processes, e.g., tumors, inflammation of lymph nodes, and plaque build-up in arteries, often afflict the human body. To treat such disease, it often is necessary to insert a medical device into the body, and to guide the medical device to the diseased site. Once the medical device is adjacent the diseased site, the medical device typically is used to photoablate or otherwise remove or reduce the diseased tissue.

As one specific example, atherosclerotic plaque is known to build-up on the walls of arteries in the human body. Such plaque build-up restricts circulation and often causes cardiovascular problems, especially when the build-up occurs in coronary arteries. Accordingly, it is desirable to detect plaque build-up and remove or otherwise reduce such plaque build-up.

Known catheters implement laser energy to remove plaque build up on artery walls. One known catheter includes a laser source and a catheter body. The catheter body has a first end and a second end, or head, and several optical fibers extend between the first end and the second end. The laser source is coupled to each of the optical fibers adjacent the catheter body first end and is configured to transmit laser energy simultaneously through the optical fibers.

To remove arterial plaque, for example, the catheter body is positioned in the artery so that the second end of the catheter body is adjacent a region of plaque build-up. The laser source is then energized so that laser energy travels through each of the optical fibers and substantially photoablates the plaque adjacent the second end of the catheter body. The catheter body is then advanced through the region to photoablate the plaque in such region.

A guide wire typically is required to properly position the catheter in the artery. The guide wire is advanced through the artery and region of plaque build-up so that it forms a path through the artery and plaque build-up. The catheter is then guided through the artery using the guide wire.

One known catheter includes ultrasound sensors positioned at its distal end for displaying images of the artery while the catheter is advanced. Known ultrasound sensors are coupled to an outer perimeter of the catheter and emit sound waves substantially radially from the catheter distal end toward the artery wall. The sound waves then are reflected by the surrounding tissue, e.g., the artery wall and plaque, and toward the ultrasound sensors. The reflected sound waves are then compared to the transmitted sound waves to generate an ultrasound image of the tissue radially sounding the distal end.

To advance the catheter, an operator first positions the catheter at a first location in the artery. Sound waves are then emitted from and received by the ultrasound sensors, and an image is then displayed showing the artery tissue adjacent the circumference of the catheter at such first location. The catheter is then advanced to a second location in the artery, and a second image is displayed showing the artery at such location. This process is then continued until the catheter is advanced through the artery and the plaque-build up.

Utilizing known ultrasound sensors as described above results in displaying images of the portions of the arterial wall which are radially disposed about the catheter, but does not provide images of the arterial wall or plaque positioned immediately forward the catheter. Particularly, and because of the reflection of the sound waves, the sensors must be aligned within the artery so that the sound waves projected toward the artery wall are substantially perpendicular to the artery wall when reflected to the sensors. Sound waves that are not perpendicular to the artery wall may provide inaccurate signals, which may result in the display of inaccurate images, which is undesirable.

Inaccurate images may result in improperly guiding the catheter through the blood vessel, which is undesirable. Particularly, known catheters must be manually inserted and guided through the blood vessel. Typically, a surgeon or other operator utilizes the displayed images to guide the catheter through the vessel and avoid damaging healthy tissue, i.e., the artery wall. If an inaccurate image displays plaque even though such tissue actually is an artery wall, it is possible that the operator may photoablate the artery wall, which is undesirable.

It would be desirable to provide a guidance system which provides improved image accuracy as compared to known catheters. It also would be desirable for such guidance system to be substantially easy to implement in connection with medical apparatus other than catheters. It further would be desirable for such guidance system to facilitate automatic advancement of the catheter through the body.

SUMMARY OF THE INVENTION

These and other objects are attained by a catheter which, in one embodiment, includes a catheter body and at least one interferometric guidance system. The catheter body includes a bundle of optic fibers, each having a first end and a second end, and the second ends of the respective optic fibers form a substantially rounded catheter head.

Each interferometric guidance system is coupled to the catheter body and includes a first optic fiber, a second optic fiber, and a detecting element. The first optic fiber of each guidance system includes a first end and a second end, and is coupled to the catheter body so that the second end is adjacent the catheter head. The second optic fiber of each guidance system similarly includes a first end and a second end, and a reference mirror is positioned adjacent the second optic fiber second end.

The detecting element of each guidance system is communicatively coupled to both the first optic fiber and the second optic fiber of such guidance system. Particularly, the first optic fiber first end is communicatively coupled to the detecting element and the second optic fiber first end is communicatively coupled to the detecting element. The detecting element is configured to determine interference between substantially equal light beams which are emitted from the same source and which are split to propagate through the first optic fiber and through the second optic fiber. The interference is then utilized to determine the density and type of tissue adjacent the catheter head, and to guide the catheter head through the tissue.

In operation, the catheter head is inserted at least partially into a blood vessel so that the catheter head and the first optic fiber second end of each guidance system is positioned in the blood vessel. The second optic fiber of each guidance system is positioned outside the blood vessel. The reference mirror of each guidance system is positioned a desired, or measuring, distance from its respective second optic fiber second end. The distances between the respective reference mirrors and optic fiber second ends may either be the same or different.

With respect to each detecting element, a light beam is split into first and second substantially equal light beams which are then transmitted through the first and second optic fibers of each guidance system, from their respective first ends to their respective second ends. The first light beam transmitted through the first optic fiber exits from the first optic fiber second end, is at least partially reflected by the tissue, re-enters the first optic fiber second end and propagates toward the first optic fiber first end. Similarly, the second light beam transmitted through the second optic fiber exits from the second optic fiber second end, is at least partially reflected by the reference mirror, re-enters the second optic fiber second end and propagates toward the second optic fiber first end.

Each detecting element detects interference between the respective reflected first light beam and the reflected second light beam and transmits interference data to a computer. The computer then utilizes the interference data to determine the density and the type of the tissue to be examined adjacent the catheter head. Particularly, the interference data is representative of the density and type of tissue located at the measuring distance from the second optic fiber second end, and the computer utilizes such data to generate an image of such tissue at such location. The computer also utilizes the interference data to control subsequent advancement of the catheter through the artery.

The above described guidance systems facilitate obtaining more accurate images than obtained using ultrasound. In addition, such systems are believed to be substantially easy to implement in connection with medical apparatus other than catheters. Furthermore, such systems are believed to facilitate automatic control and advancement of the catheter through the body.

DETAILED DESCRIPTION

Figure 1:
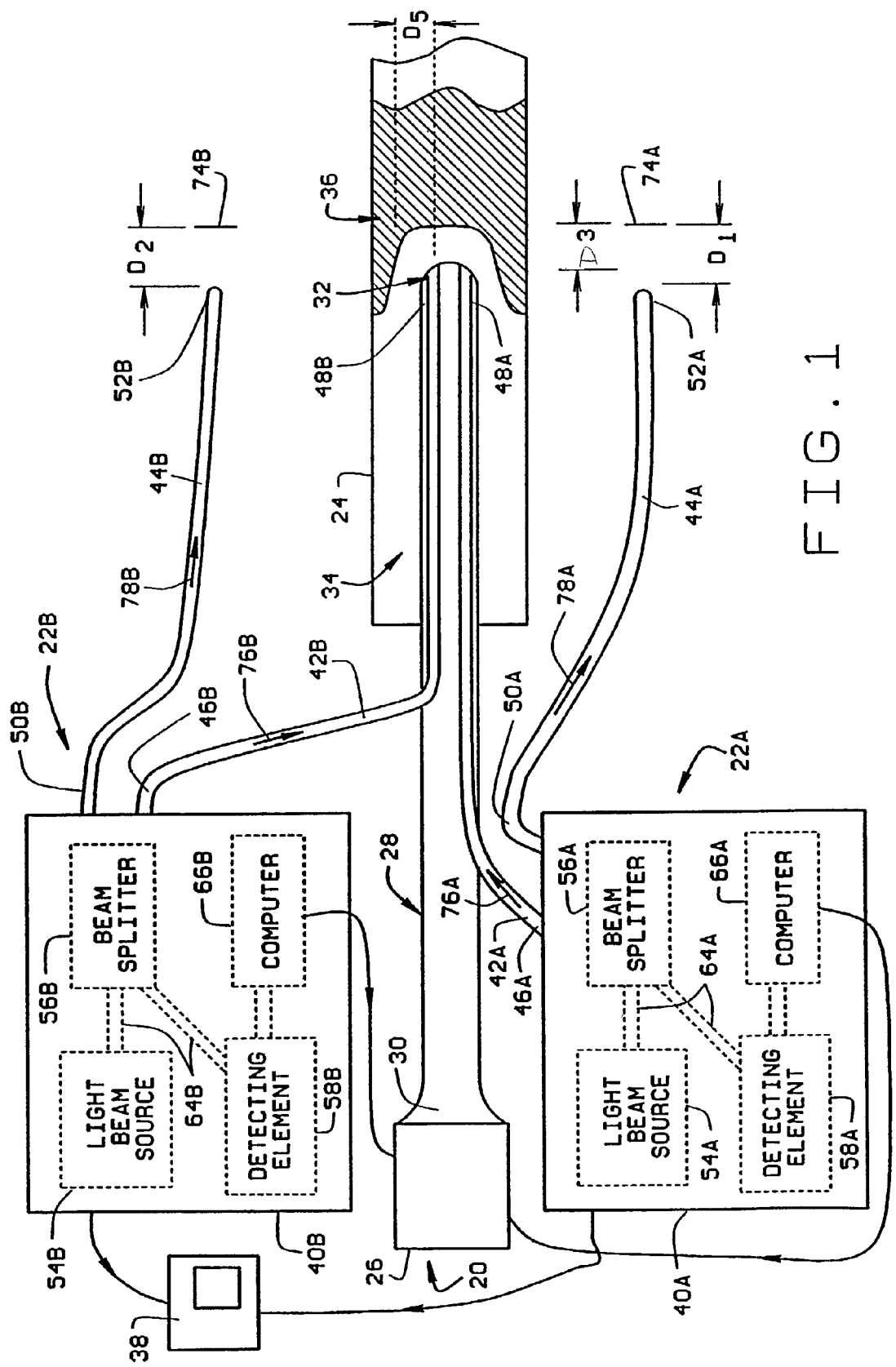
FIG. 1 is a pictorial illustration of a catheter including two guidance systems in accordance with one embodiment of the present invention inserted into a blood vessel.

FIG. 1 is a pictorial illustration of a catheter assembly 20 including two guidance systems 22A and 22B in accordance with one embodiment of the present invention inserted into a blood vessel 24 of a body. Catheter assembly 20 includes a control element 26 and a catheter body 28. Catheter body 28 has a first end 30 and a rounded, or hemispherical, second end, or head, 32, and includes a plurality of optic fibers (not shown in FIG. 1). Catheter body first end 30 is communicatively coupled to control element 26 and catheter body second end 32 is positioned within an interior 34 of blood vessel 24 adjacent tissue to be imaged, e.g., plaque 36.

Each guidance system 22A and 22B includes a respective control element 40A and 40B, a respective first, or measuring, optic fiber 42A and 42B, and a respective second, or reference, optic fiber 44A and 44B. First optic fibers 42A and 42B include respective first ends 46A and 46B and respective second ends 48A and 48B, and are coupled to catheter body 28 so that second ends 48A and 48B are adjacent catheter head 32 and are positioned in blood vessel interior 34. Second optic fibers 44A and 44B also include respective first ends 50A and 50B and respective second ends 52A and 52B. First optic fiber first end 46A and second optic fiber first end 50A are communicatively coupled to system control element 40A, and first optic fiber first end 46B and second optic fiber first end 50B are communicatively coupled to system control element 40B.

First system first optic fiber 42A is configured to emit energy waves substantially coaxially with respect to catheter head 32. Second system first optic fiber 42A is configured to emit energy waves substantially radially with respect to catheter head 32. Particularly, second end 48B of optic fiber 42B includes a prism (not shown in FIG. 1) configured to emit an energy beam at an angle with respect to catheter head 32, e.g., perpendicularly with respect to optic fiber 42A.

Each guidance system control element 40A and 40B includes a respective diagnostic light beam source 54A and 54B, a respective beam splitter 56A and 56B, and a respective detecting element 58A and 58B. Beam splitters 56A and 56B are communicatively coupled to first optic fiber first ends 46A and 46B, respectively. Similarly, beam splitters 56A and 56B are communicatively coupled to second optic fiber first ends 50A and 50B, respectively. Beam splitters 56A and 56B also are coupled to respective diagnostic light beam sources 54A and 54B and detecting elements 58A and 58B via optic fibers 64A and 64B, respectively.

Detecting elements 58A and 58B are coupled to an image screen 38 and are configured to transmit image data to image screen 38 for displaying an image of the tissue to be imaged. Detecting elements 58A and 58B also are configured to transmit control data to catheter control element 26. Particularly, detecting element 58A is configured to determine interference between a light beam propagating through first optic fiber 42A and a light beam propagating through second optic fiber 44A, and to generate interference data representative of such interference. For example, detecting element 58A may include a detector, a demodulator and an analog digitizer which cooperate in a known manner to generate such interference data. Such interference data is transmitted to a computer 66A, which generates image data for display on image screen 38 and generates control data for transmission to catheter control element 26. Similarly, detecting element 58B is configured to determine interference between a light beam propagating through first optic fiber 42B and a light beam propagating through second optic fiber 44B, and to generate interference data representative of such interference. Such interference data is transmitted to a computer 66B, which generates image data for display on image screen 38 and generates control data for transmission to catheter control element 26.

Figure 2:
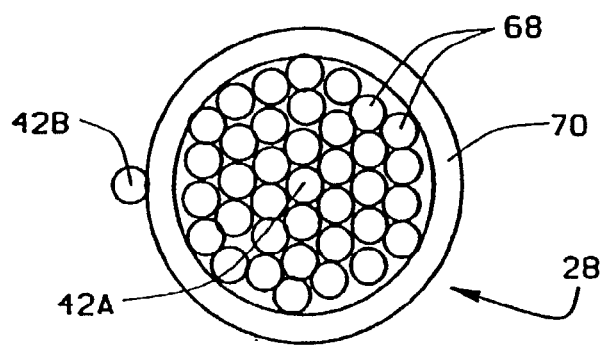
FIG. 2 is a front cross section view of the catheter body shown in FIG. 1.

Referring to FIG. 2, catheter body 28 includes several optic fibers 68 extending through a housing, or casing, 70. Second system first optic fiber 42B is coupled to housing 70 so that housing 70 extends between such second system first optic fiber 42B and catheter body optic fibers 68. First system first optic fiber 42A extends through and is substantially centered within housing 70. Alternatively, second system first optic fiber 42B may be positioned within housing 70 and first system optic fiber 42A may be positioned outside housing 70. Of course, both first system optic fibers 42A and 42B may be positioned either within housing 70 or outside housing 70.

Figure 3:
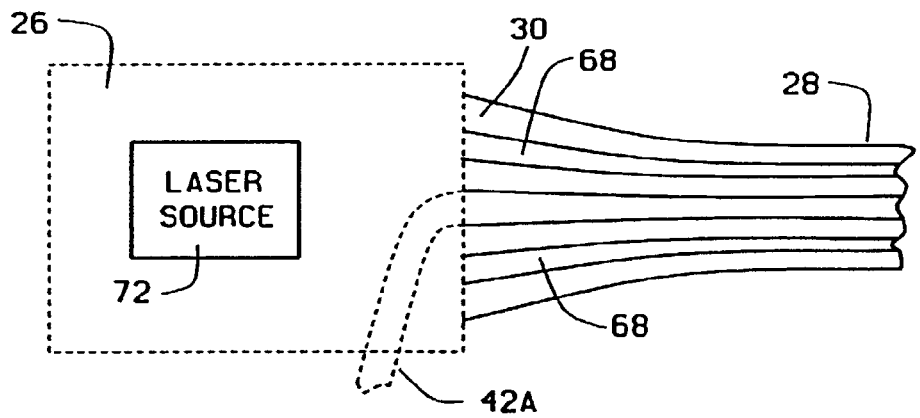
FIG. 3 is a schematic illustration of the catheter control element shown in FIG. 1.

Referring now to FIG. 3, catheter control element 26 includes a therapeutic laser source 72 substantially aligned with catheter body optic fibers 68. Laser source 70 is configured to transmit a therapeutic laser beam through catheter body optic fibers 68 for photoablating plaque 36 (FIG. 1), or other tissue.

Figure 4:
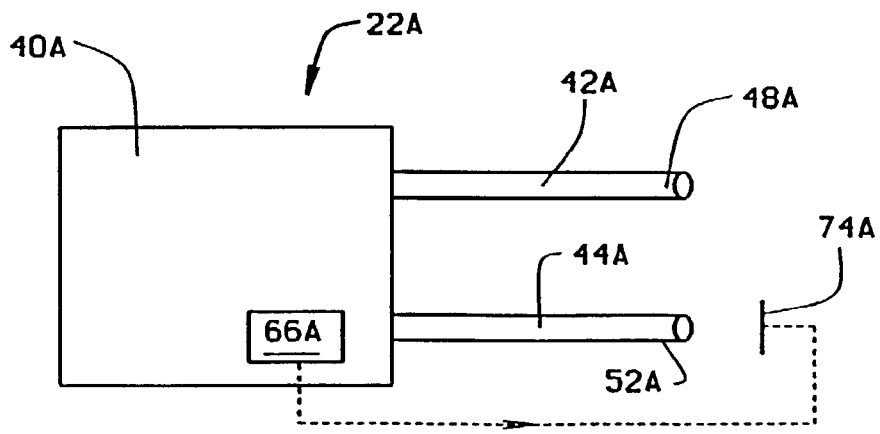
FIG. 4 is a schematic illustration of one of the guidance systems shown in FIG. 1.

Referring now to FIG. 4, guidance system 22A further includes a reference mirror 74A positioned adjacent second fiber second end 52A. Reference mirror 74A is movable with respect to second fiber second end 52A and is controlled, for example, by computer 66A. Similarly, while not shown in FIG. 4, guidance system 22B includes a reference mirror 74B positioned adjacent second fiber second end 52B. Reference mirror 74B is movable with respect to second fiber second end 52B and is controlled, for example, by computer 66B.

Prior to inserting catheter assembly 20 into blood vessel 24, each guidance system 22A and 22B is calibrated. Particularly, reference mirror 74A is positioned a distance $D_1$ from second fiber second end 52A and guidance system 22A is calibrated so that interference data obtained by detecting element 58A is representative of tissue located approximately the same distance $D_1$ from first optic fiber second end 48A. Similarly, reference mirror 74B is positioned a distance $D_2$ from second fiber second end 52B and guidance system 22B is calibrated so that interference data obtained by detecting element 58B is representative of tissue located approximately the same distance $D_2$ from first optic fiber second end 48B.

Referring again to FIG. 1, and after calibrating guidance systems 22A and 22B, catheter assembly 20 is inserted into blood vessel 24 so that catheter head 32 and first optic fiber second ends 48A and 48B are positioned within blood vessel 24, and second optic fiber second ends 52A and 52B are positioned outside blood vessel 24, and outside the body. First reference mirror 74A, as explained above, is positioned distance $D_1$ from second optic fiber second end 52A, and second reference mirror 74B is positioned distance $D_2$ from second optic fiber second end 52B.

Light beam source 54A transmits a diagnostic light beam to beam splitter 56A, which splits the light beam into first and second substantially equal light beams 76A and 78A, respectively. First light beam 76A is then transmitted through first optic fiber 42A and second light beam 78A is transmitted through second optic fiber 44A. First light beam 76A exits from first optic fiber second end 48A substantially coaxially with respect to catheter head 32, is at least partially reflected by the tissue, re-enters first optic fiber second end 48A and propagates toward first optic fiber first end 46A. Similarly, second light beam 78A transmitted through second optic fiber 44A exits from second optic fiber second end 52A, is at least partially reflected by reference mirror 74A, re-enters second optic fiber second end 52A and propagates toward second optic fiber first end 50A.

Detecting element 58A detects light interference patterns, e.g., interferences, between the reflected first light beam 76A and reflected second light beam 78A, and transmits interference data representative of such interferences to computer 66A. Computer 66A utilizes the interference data to determine the type and depth of the tissue located at a distance $D_3$ from first optic fiber second end 48A. Particularly, computer 66A utilizes the interference data to determine what type of tissue, if any, is located at a distance $D_3$ from first fiber second end 48A, where distance $D_3$ is substantially the same as distance $D_1$. For example, computer 66A may include a memory, and representative interference signals for different types of tissues, e.g., plaque, artery walls, healthy tissue, cancerous tissue, may be stored in such memory. Computer 66A compares the interference data received from detecting element 58A to such stored representative interference signals to determine the type of tissue located distance $D_3$ from first fiber second end 48A. Distances $D_1$ and $D_3$ may, for example, be less than or equal to 1 millimeter, e.g., one quarter of a millimeter. Of course, distances $D_1$ and $D_3$ may be larger than 1 millimeter.

If desired, reference mirror 74A may be moved with respect to second fiber second end 48A to recalibrate guidance system 22A while it is positioned in a blood vessel 24. Particularly, if detecting element 58A generates interference data representative of a loss of signal through first optic fiber 42A, reference mirror 74A may be moved to reestablish a signal at a distance $D_4$ (not shown in FIG. 1) which is different from distance $D_1$.

Similarly, and in yet another alternative, reference mirror 74A may be moved with respect to second fiber second end 48A to determine the type and depth of the tissue located at a varying distances from second fiber second end 48A. Particularly, reference mirror 74 may be moved between a point immediately adjacent second fiber second end 48A and a point distance $D_1$ from second fiber second end 48A to determine the type and depth of the tissue located at each point between such two points. Accordingly, reference mirror 74A may be moved to determine tissue type at multiple different distances from second fiber second end 48A.

Computer 66A generates image data of such tissue and displays the image of such tissue on image screen 38. Particularly, computer 66A utilizes the interference data generated at various points in the tissue to generate image data representative of a substantially linear image profile of the examined tissue. Computer 66A also utilizes the interference data to generate and transmit control signals to catheter control element 26, as is described in more detail below.

Similarly, light beam source 54B transmits a diagnostic light beam to beam splitter 56B, which splits the light beam into first and second substantially equal light beams 76B and 78B, respectively. First light beam 76B is then transmitted through first optic fiber 42B and second light beam 78B is transmitted through second optic fiber 44B. First light beam 76B exits from first optic fiber second end 48B substantially radially with respect to catheter head 32, is at least partially reflected by the tissue, re-enters first optic fiber second end 48B and propagates toward first optic fiber first end 46B. Similarly, second light beam 78B transmitted through second optic fiber 44B exits from second optic fiber second end 52B, is at least partially reflected by reference mirror 74B, re-enters second optic fiber second end 52B and propagates toward second optic fiber first end 50B.

Detecting element 58B detects interference between the reflected first light beam 76B and reflected second light beam 78B, and transmits interference data representative of such interference to computer 66B. Computer 66B utilizes the interference data, as described above, to determine the type of tissue located a distance $D_5$ between the tissue and first optic fiber second end 48B, where distance $D_5$ is substantially the same as distance $D_2$. Computer 66B, utilizing the interference data, generates image data of such tissue, as described above, and displays the image on image screen 38. Computer 66B also utilizes the interference data to generate and transmit control signals to catheter control element 26, as is described in more detail below.

If the tissue located at distance $D_3$ and $D_5$ is, for example, plaque 36, then catheter assembly 20 may be utilized to photoablate plaque 36. Particularly, computers 66A and 66B may transmit control signals to control element 26 so that control element 26 energizes laser source 72 to transmit a laser beam through catheter body optic fibers 68. The laser beam propagates through catheter body optic fibers 68 and photoablates the plaque 36 in a known manner.

Alternatively, computers 66A and 66B may transmit control signals to control element 26 so that control element 26 energizes laser source 72 to transmit a laser beam through only selected catheter body optic fibers 68. For example, if interference data obtained at first system detecting element 58A indicates that the tissue in front of catheter head 32 is plaque 36, and if second system detecting element 58B indicates that the tissue adjacent second system first optic fiber 42B is an artery wall, then control element may transmit a laser beam only through optic fibers 68 adjacent first system first optic fiber 42B, and not through optic fibers 68 adjacent second system first optic fiber 42A.

To facilitate determining accurate tissue depth and tissue type during blood vessel 24 movement, e.g., if blood vessel 24 is located in the heart, where blood vessel 24 may move relative to catheter head 32 even if catheter head 32 is not advanced through blood vessel 24, guidance systems 22A and 22B may be configured to determine tissue type and density at only periodic intervals. For example, if blood vessel 24 is located in the heart, and it is not practical to stop the heart, then computers 66A and 66B may be configured to sample interference data from respective detecting elements 58A and 58B at a same period of time of the cardiac cycle. Particularly, computers 66A and 66B may be communicatively coupled to an EKG and configured to sample interference data only at the top of the R wave. Alternatively, computers 66A and 66B may be communicatively coupled to an EKG and configured to sample interference data only at the middle of the T wave. Of course, computers 66A and 66B may be configured to sample interference data at other periodic intervals.

The above described catheter and guidance systems facilitate obtaining higher resolution images than obtained using ultrasound. Such guidance systems also are believed to be substantially easy to fabricate and utilize in connection with a catheter such as catheter assembly 20.

In an alternative embodiment, the second optic fiber second end prism may be configured to emit first light beam 76B angularly with respect to an axis of first optic fiber 42B but not perpendicularly with respect to such axis. Accordingly, images may be obtained of tissue about a circumference of catheter head 32, rather than merely the tissue positioned coaxially with catheter head 32 or radially with respect to catheter head 32.

In addition, and in accordance with yet another embodiment of the present invention, a catheter may be utilized in connection with several, e.g., five, guidance systems 22. The guidance systems 22 may be positioned so that respective measuring, or first optic fibers, are positioned to emit light beams coaxially with respect to the catheter head, as well as substantially about the entire circumference of the catheter head.

In still yet another embodiment of the present invention, measuring fibers 42A and 42B are configured to transmit both diagnostic light beams from respective diagnostic light beam sources 54A and 54B and therapeutic laser beams from therapeutic laser source 72. Particularly, measuring fiber 42A is communicatively coupled to both light beam source 54A and laser source 72. Similarly, measuring fiber 42B is communicatively coupled to both light beam source 54B and laser source 72. Laser source 72 and light beam sources 54A and 54B may be configured to transmits beams having different wave lengths to facilitate simultaneous transmission of both the therapeutic laser beam and diagnostic light beams through measuring fibers 42A and 42B.

Guidance systems 22A and 22B may also be implemented in connection with medical apparatus other than catheters. For example, guidance systems 22A and 22B may be coupled to a medical apparatus such as an angioplasty balloon or an atherectomy device. Similarly, guidance systems 22A and 22B may be utilized in connection with hollow tubes configured to facilitate localized treatment. For example, guidance systems 22A and 22B may be utilized to position a hollow tube adjacent a region so that medicine, radiation, or energy may be transmitted directly to such region. Similarly, guidance systems 22A and 22B may be utilized to facilitate positioning biopsy devices proximate desired sites.

Guidance systems 22A and 22B also facilitate automatic control of the advancement of catheter assembly 20 through blood vessel 24. Particularly, and in accordance with still yet another embodiment, guidance systems 22A and 22B are coupled to a motor (not shown) which is coupled to catheter body 28. The motor is configured to advance catheter body 28 through the body and to receive control signals from respective computers 66A and 66B. If respective computers 66A and 66B transmit control signals indicating that the tissue adjacent catheter head 32 is, for example, plaque, then the motor advances catheter head 32 through the plaque. If, however, computers 66A and 66B transmit control signals indicating that the tissue adjacent catheter head 32 is, for example, a normal artery wall, then the motor stops advancing catheter head 32.

From the preceding description of the present invention, it is evident that the objects of the invention are attained. Although the invention has been described and illustrated in detail, it is to be clearly understood that the same is intended by way of illustration and example only and is not be taken by way of limitation. For example, while the guidance system was described in connection with a catheter having a rounded head, such system may be utilized in connection with a catheter having a different shaped, e.g., a spherical, or an angular, head. In addition, while the guidance systems included diagnostic light sources configured to emit a light beam, such light sources may be configured to emit any coherent light beam, such as laser light or polarized light. Furthermore, while each guidance system was described in connection with its own computer, the guidance systems may be coupled to one computer. Accordingly, the spirit and scope of the invention are to be limited only by the terms of the claims.

What is claimed is:

1. A method for guiding a medical instrument having a first end and a second end through a blood vessel, said method comprising the steps of:

coupling at least one guidance system to the medical instrument, the guidance system including a first optic fiber having a first end and a second end and configured to propagate a sampling light beam, a second optic fiber having a first end and a second end and configured to propagate a reference light beam, a reference mirror positioned adjacent the second optic fiber second end, and a detecting element communicatively coupled to the first ends of the first and second optic fibers;

placing the second end of the first optic fiber adjacent the second end of the medical instrument;

configuring the second end of the medical instrument to direct the sampling light beam substantially coaxially with respect to the second end of the medical instrument;

inserting the medical instrument at least partially into the blood vessel; and utilizing the detecting element configured to determine interference between a light beam propagating through the first optic fiber and a light beam propagating through the second optic fiber to guide the medical instrument through the blood vessel.

2. A method in accordance with claim 1 wherein the medical instrument is a catheter having a catheter head, and wherein inserting the medical instrument at least partially into the blood vessel comprising the step of inserting the catheter head into the blood vessel.

3. A method in accordance with claim 1 wherein coupling at least one guidance system to the medical instrument comprises the step of coupling at least two guidance systems to the medical instrument.

4. A method in accordance with claim 1 wherein coupling at least one guidance system to the medical instrument comprises the step of coupling five guidance systems to the medical instrument.

5. A method in accordance with claim 1 wherein the medical instrument is a catheter.

6. A method in accordance with claim 1 wherein the medical instrument is an angioplasty balloon.

7. A method in accordance with claim 1 wherein the medical instrument is an atherectomy device.

8. A method in accordance with claim 1 wherein the medical instrument is a biopsy device.

9. A method in accordance with claim 1 wherein the medical instrument is a hollow tube.

10. A method in accordance with claim 1 wherein utilizing the detecting element configured to determine interference comprises the step of generating an image of tissue adjacent the medical instrument.

11. A method in accordance with claim 10 wherein said image is a linear profile image of the tissue adjacent the medical instrument.

12. A method in accordance with claim 10 comprising the step of generating an image of tissue coaxially aligned with the medical instrument.

13. A method in accordance with claim 1 wherein utilizing the detecting element configured to determine interference comprises the step of automatically controlling the medical instrument.

14. A method in accordance with claim 1 further comprising the step of utilizing ultrasound for imaging at least portions of the blood vessel.

* * * * *